United States Patent [19]

Murdock

[11] 4,059,098
[45] Nov. 22, 1977

[54] FLEXIBLE ULTRASOUND COUPLING SYSTEM

[75] Inventor: David M. Murdock, Palo Alto, Calif.

[73] Assignee: Stanford Research Institute, Menlo Park, Calif.

[21] Appl. No.: 597,413

[22] Filed: July 21, 1975

[51] Int. Cl.² .............................................. A61B 10/00
[52] U.S. Cl. ..................................... 128/2 V; 73/570; 128/2.05 Z
[58] Field of Search ............... 128/2 V, 2.05 Z, 24 A; 73/67.7–67.9

[56] References Cited

U.S. PATENT DOCUMENTS

| | | | |
|---|---|---|---|
| 2,283,285 | 5/1942 | Pohlman | 128/24 A |
| 2,545,101 | 3/1951 | Meunier | 128/24 A X |
| 2,559,227 | 7/1951 | Rieber | 128/24 A |
| 2,789,557 | 4/1957 | Davis, Jr. | 128/24 A |
| 3,237,623 | 3/1966 | Gordon | 128/24 A |
| 3,269,173 | 8/1966 | Von Ardenne | 128/2 V X |
| 3,356,086 | 12/1967 | Behney | 128/24 A |
| 3,480,002 | 11/1969 | Flaherty et al. | 128/2 V |
| 3,821,891 | 7/1974 | Collins et al. | 128/2 V X |

FOREIGN PATENT DOCUMENTS

| | | | |
|---|---|---|---|
| 654,673 | 12/1937 | Germany | 128/24 A |
| 824,683 | 12/1951 | Germany | 128/24 A |

*Primary Examiner*—Kyle L. Howell
*Attorney, Agent, or Firm*—Urban H. Faubion

[57] ABSTRACT

Essentially nonreflective coupling for ultrasonic waves is provided between a fluid medium confined in a rigid container and a biological specimen, such as a human body, through a container closing bellows system which incorporates a thin, flexible closing membrane that contacts and conforms to the contours of the specimen. A supportive bellows system between rigid parts of the fluid container and the membrane gives the membrane the essential properties of conforming to the contours of a specimen having variations in curvature (concavities and convexities) while having the ability to contain the fluid medium without rupture or undue distension when it is not supported externally, as by contact with the specimen. The supportive bellows system utilizes a pair of flexible toroidal members, one tubular and one U-shaped in cross section, attached to one another in series and having internal venting so that pressure within the toroids is governed by the pressure of the fluid inside the coupling bellows system. The container closing bellows system is fluid filled, the flexible closing membrane is tautly stretched over the tubular toroid member so that it is supported by the bellows system and forms a fluid-tight closure, and a vent means is provided to adjust pressure inside the said container closing bellows system.

14 Claims, 3 Drawing Figures

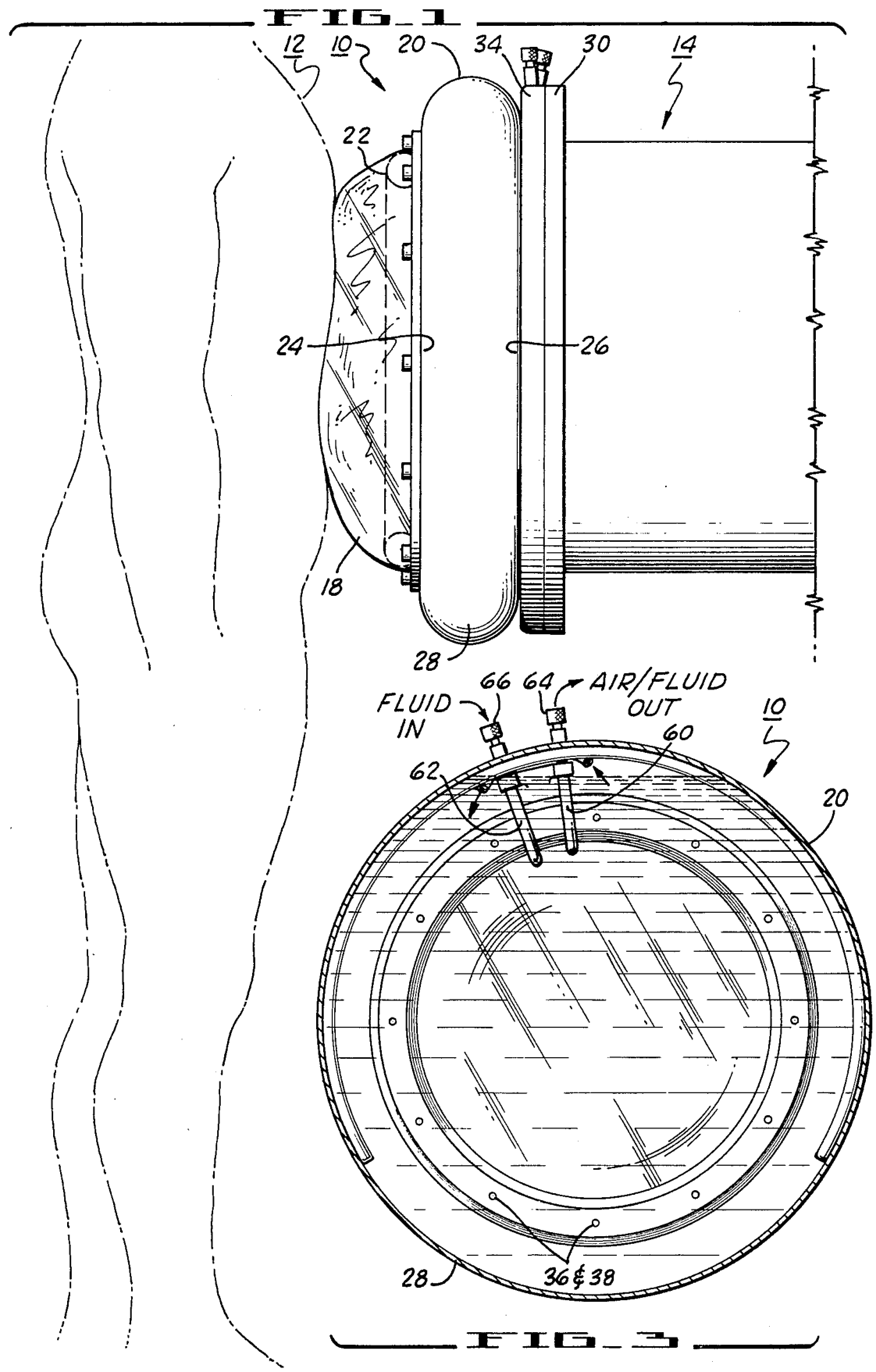

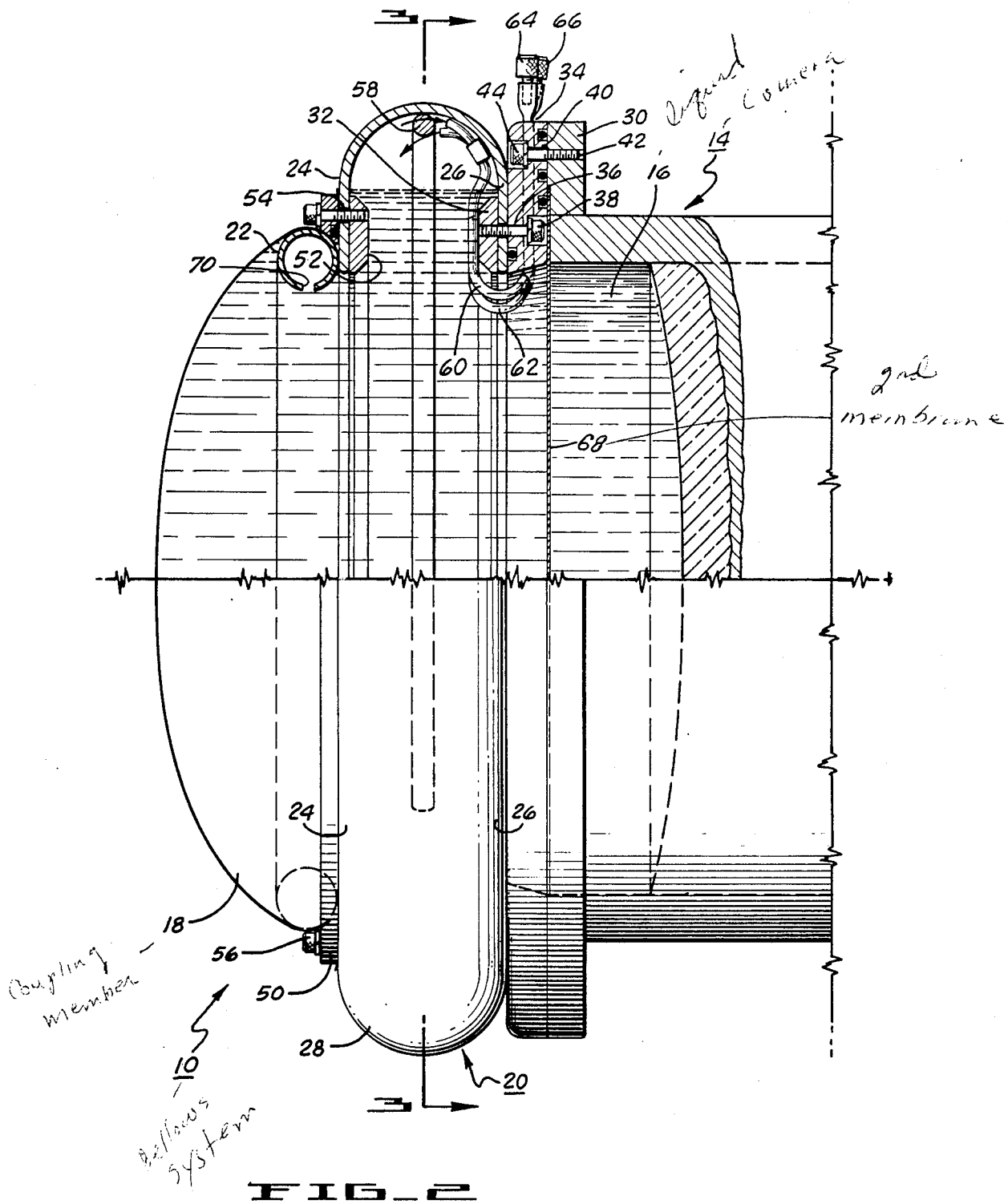
FIG_2

– 4,059,098 –

FLEXIBLE ULTRASOUND COUPLING SYSTEM

ORIGIN OF INVENTION

The invention described herein was made in the course of work under a grant or award from the Department of Health, Education and Welfare.

BACKGROUND OF INVENTION

This invention is applicable to acoustic imaging for nondestructive testing and is particularly useful in biomedical applications for acoustic imaging of internal organs of living beings in real time. For real time ultrasonic imaging of organs in a living organism, for example, the heart in a living human body, it is important that acoustic waves be coupled to and from the specimen with a minimum loss at the interface between the specimen and the transmitter and receiver. In order to pass the acoustic waves with a minimum of reflection at the interface with the specimen, it is necessary that the coupling conform to the contours of the specimen, which contours may be highly complex. The coupling arrangement is particularly suitable for use in a system wherein the ultrasonic waves are to pass between the specimen and an ulttasonic transmitting and/or receiving system which is contained, at least partially, in a fluid medium. Thus, the coupling also serves as a closure or barrier to contain the liquid within the liquid filled container.

SUMMARY AND OBJECT OF INVENTION

The present invention meets all of the above requirements by providing an essentially nonreflective coupling of ultrasonic waves between a fluid medium confined in a rigid container and a biological specimen by providing a container closing bellows system. A very thin, flexible membrane is provided to interface with the specimen, which membrane conforms to the surface shape of the specimen. In order to support the very thin, flexible membrane in such a way that it will not rupture or be unduly distended by the pressure of the fluid medium inside the container, a supportive bellows system is incorporated between the rigid parts of the fluid container and the membrane. The bellows system incorporates a pair of flexible toroidal members attached to one another in series and having internal venting, so that pressure within the toroids is governed by the pressure of the fluid inside the coupling system. In a preferred embodiment a second membrane, preferably of heavier gauge than the membrane which is to interface with the specimen, is provided at the opposite end of the bellows system to act as a barrier between the bellows and the container, and means is provided to adjust pressure inside the bellows system.

The novel features which are believed to be characteristic of the invention are set forth with particularity in the appended claims. The invention itself, however, both as to its organization and method of operation, together with further objects and advantages thereof, may best be understood by reference to the following description taken in connection with the accompanying drawings.

BRIEF DESCRIPTION OF DRAWINGS

FIG 1 is a side elevation showing the coupling arrangement attached to one end of an ultrasonic camera (broken away) positioned to examine a subject (represented here as a human body);

FIG. 2 is a partially broken away side elevation of the nonreflective coupling system as illustrated in FIG. 1, showing details both of the coupling system and of how it is applied to a portion of an ultrasonic camera; and FIG. 3 is an end view, in section, of the coupling arrangement of FIGS. 1 and 2 and taken along section lines 3—3 of FIG. 2.

DESCRIPTION OF PREFERRED EMBODIMENTS

The invention is illustrated and described here in its most exacting application, viz., as a coupling for an ultrasonic camera of the image conversion type which is used primarily to image internal structures in a living human body. As a consequence, the coupling and closing bellows system 10 is illustrated in FIG. 1 in place against a human body 12 and is shown attached to the front of the cylindrical body 14 of such a camera. Functionally, the bellows system 10 serves to seal the camera body 14 and thereby confine a liquid 16 therein (see FIG. 2) and to couple ultrasonic waves between the camera 14 and the specimen 12. Since the camera itself is not a part of the present invention, it is not illustrated in detail here. Details of the camera can be found in copending applications Philip S. Green, Focusing and Deflecting System for Acoustic Imaging, Ser. No. 354,236, filed Apr. 25, 1973, now U.S. Pat. No. 3,913,061 and Philip S. Green et al., Ultrasonic Camera System and Method, Ser. No. 411,729, filed Nov. 1, 1973 now U.S. Pat. No. 3,937,066. The subject matter of these applications is incorporated herein by reference.

In order to minimize reflections at the interface between the coupling bellows system 10 and the specimen 12 and also to form a liquid seal, a thin, flexible coupling membrane 18 (here a polyurethane membrane 1 mil thick) is stretched over the front of the bellows system 10. Unless special supporting structure is provided, such a thin membrane will not support the weight of the liquid confined in the camera without undue physical distension or rupture when not supported by contact with the specimen. The necessary supporting structure includes a pair of flexible but relatively stiff toroidal members 20 and 22 which form the transition between the front end of the camera housing 14 and the outer coupling membrane 18. The first flexible toroidal member 20 has a U-shaped cross section with two opposing side walls 24 and 26 and an outer wall portion 28 joining them. For the particular application of common 12½ by 2¼ vehicle tire made by Michelin is used, thus the toroidal member 20 has both flexibility and firmness. In practical embodiment, the secondary supporting toroidal member 22 constitutes a firm neoprene tube bent into the toroidal shape. The second flexible toroidal member 22 is vented internally so that it also contains the fluid medium of the bellows and for this purpose openings such as shown at 70 in FIG. 2 may be provided as would be obvious to one skilled in the art.

As illustrated, the mechanical means for securing the bellows system to the front of the camera includes an annular ring 30 rigidly but removably secured around the front end of the cylindrical camera body 14. Any conventional means of securing the annular ring 30 to the front of the camera body 14 may be used. In order to hold the primary toroidal bellows member 20 on the front of the camera body 14, a pair of wall supporting annular retaining rings 32 and 34 is provided. One of the rings, internal supporting and retaining ring 32, is provided just inside the outer side wall portion 26 of the main toroidal member 20 which is adjacent the camera body 14, and the other retaining ring 34 is provided outside this side wall portion 26, so that the side wall portion 26 is sandwiched between the two retaining rings 32 and 34. The inner diameters of the inner and outer retaining rings 32 and 34 are approximately the same, whereas the outer ring 34 has an outside diameter which approximately matches that of the bellows supporting retaining ring 30 on the outside of the camera body 14. The inner and outer side wall retaining rings 32 and 34 are provided with a plurality of equally spaced registered bolt receiving apertures 36 so that a series of bolts 38 may be passed through the retaining rings 32 and 34 as well as the outer side wall portion 26 included therebetween, thus holding the side wall portion 26 firmly between the inner and outer retaining rings.

The apertures 36 in the outer retaining ring 34 (see FIG. 2) are countersunk to receive the heads of the securing bolts 38 so that the bolt heads do not interfere with assembly. The outer retaining ring 34 is also provided with a similar series of apertures 40 near its outer periphery which match a corresponding series of apertures 42 in the bellows supporting retaining ring 30 on the end of the cylindrical camera body 14. The outer retaining ring 34 is thus secured to the camera body 14 by a series of bolts 44 which extend through the outer retaining ring 34 and are threaded into the retaining ring 30 on the camera body 14. As a practical matter, sealing O rings are provided in annular grooves around the outer face of the outer retaining ring and also in a groove around the opposite face adjacent the outer wall portion of the supported toroidal member. In this manner the coupling and sealing bellows system 10 is secured to the front of the camera 14. For practical reasons the O ring seals and grooves are not given reference numerals. All of the metal parts are made of materials which are inert to the fluid contained in the system; for example, the retaining rings are stainless steel.

It has been found that without further supportive means, both the first toroidal member 20 and the thin polyurethane membrane 18 have a tendency to become deformed and droop under pressure of the included liquid. As a consequence, the second supportive toroidal member 22 is secured to the opposite side wall portion 24 of the first toroidal member 20 to provide additional support for the thin flexible coupling membrane 18. As previously indicated, the second flexible toroidal member 22 constitutes a neoprene tube formed into a torus. The inner diameter of the smaller toroidal member 22 is approximately the same as the inner diameter of the side wall portions 24 and 26 of the primary supporting toroidal member 20. The second supporting toroidal member 22 is held in place adjacent the outer side wall portion of the primary toroidal member 20 by cooperation of the thin flexible coupling membrane 18 and a pair of retaining rings 50 and 52 which are used to secure the coupling membrane 18 in place. Of the pair of membrane securing annular rings 50 and 52, the ring 52 inside the primary toroidal member 20 is similar to the inner supporting ring 32 inside the opposite side wall 26. The outer membrane supporting annular ring 50 has an outside diameter which approximately matches the outside diameter of the inner ring 52 and has its inner diameter shaped (dished or radiused) to receive the supportive membrane holding toroidal member 22. The inner and outer annular membrane retaining rings 52 and 50, respectively, are provided with a plurality of matching bolt receiving apertures 54. The thin, flexible membrane 18 is stretched tightly over the outer periphery of the supportive toroidal member 22 and up along the adjacent side wall portion 24 of the primary toroidal member 20. The outer membrane supporting retaining ring 50 is placed in proper register over the thin membrane and bolted to the inner membrane retaining ring (by bolts 56) to provide a liquid tight seal. Note that the outer retaining ring 50 is provided with an annular groove (not numbered) around its inner face which holds an O ring seal (also not numbered).

In order to introduce a fluid inside the sealed front part of the camera and the coupling bellows system, the outer retaining ring 34 for the primary toroidal member 20 which is affixed to the front of the camera 14 is provided with a pair of apertures therethrough, and a pair of tubes 60 and 62 extends through the apertures, around the inner periphery of the adjacent side wall portion 26 and up into the open portion of the U-shaped toroidal member near the top wall portion 28. When the tubes 60 and 62 are open, one of them, e.g., 62, may be used to introduce fluid while the other, e.g., 60, will provide an air outlet so that the otherwise closed system can be fluid filled. In practice it has been found that distension of the flexible membrane 18 is reduced or eliminated by adjusting the pressure inside the bellows system utilizing the air/fluid inlet and outlet tubes 60 and 62 which are sealed by a pair of bolts 64 and 66 threaded into the outer ends thereof. One way to adjust the internal pressure is to compress the bellows system 10 while one or both of the air/fluid inlet and outlet tubes is open, seal the tubes, and then relieve the compression. This forms a negative pressure in the bellows system. As an additional means of supporting the bellows system 10 and preventing the top wall portion 28 of the primary supporting toroidal member 20 from collapsing (flattening due to the pressure differential—positive outside pressure to negative internal pressure), a stainless steel rod 58 is bent to fit the inner periphery of the outer side wall 28 of the primary bellows member 20.

While the supportive bellows sealing and coupling system 10 works well as described thus far, it has also been found that its performance is improved somewhat by the addition of a membrane 68 which extends over the end of the cylindrical camera housing 14 and forms a completely closed bellows system. In the embodiment illustrated the second membrane 68 may be thicker than the flexible coupling membrane 18 on the opposite side of the bellows system 10, but it should be of a material, such as Mylar (trademark of du Pont), which is essentially transparent to ultrasonic energy in the environment. In the embodiment illustrated the inner membrane 68 is held in place between the outer side wall supporting and retaining ring 34 and the retaining ring 30 which surrounds the end of the camera 14. In this manner, when the coupling and closing bellows system 10 is removed from the end of the camera, it forms a self-contained unit.

Thus, it is seen that the bellows coupling and closing unit on the front of the camera 14 supports the flexible coupling membrane 18 so that it may be moved into position against a specimen's body 12 and will conform closely to relatively complex shapes in such a way that pressure against the specimen is not uncomfortable. At the same time the bellows coupling and closing unit supports the very thin, flexible membrane 18 in such a manner that it does not rupture or become unduly distended under the weight and pressure of the fluid 16 contained therein.

While a particular embodiment of the invention is illustrated and described, the invention is not limited to the specific configuration, since modifications may be made utilizing the principles taught without departing from the inventive concepts. It is contemplated that the appended claims will cover any such modifications as may fall within the true spirit and scope of the invention.

What is claimed is:

1. A coupling and closing system for coupling ultrasonic waves even through substantially horizontal coupling paths between a fluid medium contained in a rigid container and a specimen and for confining the fluid medium, said system comprising a flexible supporting bellows system to be fixed at one end over a fluid opening to the rigid container and including:
   a first toroidal member of relatively firm but flexible material having first and second opposing side wall portions and an outer peripheral joining and sealing wall portion and being vented to provide fluid communication inside the coupling and closing system;
   means for securing one of the side wall portions of said first toroidal member over a fluid opening to the rigid container;
   a second flexible ztoroidal member also of relatively firm but flexible material juxtaposed to the first toroidal member and having first and second opposing side wall portions and at least one joining sealing wall portion and being vented to provide fluid communication inside the coupling and closing system;
   a thin flexible membrane transparent to ultrasonic waves for closing the supportive bellows system; and
   means for securing said flexible membrane over said second toroidal member in fluid-tight relation to the outside of the said second one of the said side wall portions of said first toroidal member;
   said thin, flexible membrane being stretched over at least the joining sealing wall portion and the one of said sidewalls of the second flexible toroidal member adjoining the first toroidal member for securely holding the second flexible toroidal member in juxtaposed relation to said first toroidal member and for forming a fluid tight closure for the said supportive bellows system.

2. A coupling and closing system as defined in claim 1 wherein means is provided to adjust the pressure within the said coupling and closing system.

3. A coupling and closing system as defined in claim 1 wherein said first flexible toroidal member has a U-shaped cross section whereby the legs of said U form the side wall portions and the bottom of the said U defines the said outer peripheral joining and sealing wall, with the said U opened to the inside of said coupling and closing system to form the said vent around the inner periphery and thereby receive any fluid.

4. A coupling and closing system as defined in claim 3, wherein said second toroidal member has a circular cross section.

5. A coupling and closing system as defined in claim 4, wherein a stiffening rod defining at least a portion of a toroid is positioned inside said first toroidal member in such a manner as to support the said outer peripheral wall portion and thus prevent collapse thereof under the weight of any fluid within the said coupling and closing system.

6. A coupling and closing system as defined in claim 3 wherein a stiffening rod defining at least a portion of a toroid is positioned inside said first toroidal member in such a manner as to support the said outer peripheral wall portion and thus prevent collapse thereof under the weight of any fluid within the said coupling and closing system.

7. A coupling and closing system as defined in claim 1 wherein a stiffening rod defining at least a portion of a toroid is positioned inside said first toroidal member in such a manner as to support the outer peripheral wall portion and thus prevent collapse thereof under the weight of any fluid within the said coupling and closing system.

8. A coupling and closing system for coupling ultrasonic waves even through substantially horizontal coupling paths between a fluid medium contained in a rigid container and a specimen and confining the fluid medium in the container, comprising a flexible supportive bellows system, a pair of thin, flexible closing membranes separated and supported by the said flexible bellows system to form a fluid-tight closure, and a fluid substantially filling the said fluid-tight closure, said supportive bellows system including
   a first toroidal member of relatively firm but flexible material having first and second opposing side wall portions and a joining and sealing wall portion, and being vented around its inner periphery to receive any fluid inside the coupling and closing system, means for securing said first side wall portion in fluid-tight relation to the rigid container; and
   a second toroidal member also of relatively firm but flexible material having first and second opposing side wall portions and at least one joining and sealing wall portion, said second toroidal member being juxtaposed to said first toroidal member and being vented to provide fluid communication inside the said coupling and closing system and means including one of the thin flexible closing membranes for securing the first one of the side wall portions of said second toroidal member to the said second one of the said side wall portions of said first toroidal member in juxtaposed fluid-tight relation.

9. A coupling and closing system as defined in claim 8, wherein means is provided to adjust the pressure within the said coupling and closing system.

10. A coupling and closing system as defined in claim 8, wherein said first flexible toroidal member has a U-shaped cross section, with the said U opened inwardly to form the said vent around the inner periphery and thereby receive any fluid within said coupling and closing system.

11. A coupling and closing system as defined in claim 10, wherein a stiffening rod defining at least a portion of a toroid is positioned inside said first toroidal member in such a manner as to support the outer peripheral wall portion and thus prevent collapse thereof under the weight of any fluid within said coupling and closing system.

12. A coupling and closing system as defined in claim 11, wherein said second toroidal member has a circular cross section.

13. A coupling and closing system as defined in claim 12, wherein a stiffening rod defining at least a portion of a toroid is positioned inside said first toroidal member in such a manner as to support the outer peripheral wall portion and thus prevent collapse thereof under the weight of any fluid within said coupling and closing system.

14. A coupling and closing system as defined in claim 8, wherein a stiffening rod defining at least a portion of a toroid is positioned inside said first toroidal member in such a manner as to support the outer peripheral wall portion and thus prevent collapse thereof under the weight of fluid therein.

* * * * *